United States Patent
Galpin et al.

(10) Patent No.: US 11,969,495 B2
(45) Date of Patent: Apr. 30, 2024

(54) SULPHATE-FREE AND NONIONIC SURFACTANT-FREE CLEANSING COMPOSITION

(71) Applicant: Conopco, Inc., Englewood Cliffs, NJ (US)

(72) Inventors: Annie Jaye Galpin, Mancot (GB); Robert Machen, Prenton (GB); Smita Puntambekar, Wirral (GB); Robert George Riley, Chester (GB); Pierre Starck, Chester (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 762 days.

(21) Appl. No.: 17/052,965

(22) PCT Filed: May 7, 2019

(86) PCT No.: PCT/EP2019/061752
§ 371 (c)(1),
(2) Date: Nov. 4, 2020

(87) PCT Pub. No.: WO2019/215201
PCT Pub. Date: Nov. 14, 2019

(65) Prior Publication Data
US 2021/0128447 A1 May 6, 2021

(30) Foreign Application Priority Data

May 11, 2018 (EP) ..................................... 18171879

(51) Int. Cl.
| | | |
|---|---|---|
| *C11D 1/28* | (2006.01) | |
| *A61K 8/04* | (2006.01) | |
| *A61K 8/20* | (2006.01) | |
| *A61K 8/368* | (2006.01) | |
| *A61K 8/44* | (2006.01) | |
| *A61K 8/46* | (2006.01) | |
| *A61K 8/73* | (2006.01) | |

(Continued)

(52) U.S. Cl.
CPC .................. *A61K 8/89* (2013.01); *A61K 8/04* (2013.01); *A61K 8/20* (2013.01); *A61K 8/368* (2013.01); *A61K 8/442* (2013.01); *A61K 8/466* (2013.01); *A61K 8/737* (2013.01); *A61Q 5/02* (2013.01); *A61K 2800/30* (2013.01); *A61K 2800/596* (2013.01)

(58) Field of Classification Search
CPC .... C11D 1/28; C11D 1/90; C11D 1/92; C11D 1/94; C11D 3/0094; C11D 3/37; C11D 3/3738; C11D 9/36; C11D 17/0021
See application file for complete search history.

(56) References Cited

U.S. PATENT DOCUMENTS

| | | |
|---|---|---|
| 4,726,915 A | 2/1988 | Verdicchio |
| 5,811,084 A | 9/1998 | Busch, Jr. et al. |
| 5,811,087 A | 9/1998 | Mohring et al. |

(Continued)

FOREIGN PATENT DOCUMENTS

| | | |
|---|---|---|
| CN | 107519031 | 12/2017 |
| CN | 107530243 | 1/2018 |

(Continued)

OTHER PUBLICATIONS

Search Report and Written Opinion in EP18171879; dated Nov. 12, 2018.

(Continued)

*Primary Examiner* — Charles I Boyer
(74) *Attorney, Agent, or Firm* — Foley & Lardner LLP

(57) ABSTRACT

1. A sulphate free cleansing composition for hair and scalp comprising, in an aqueous continuous phase: a total amount of anionic surfactant, amphoteric surfactant and zwitterionic surfactant consisting of: (i) from 3 wt % to 13 wt %, by weight of the total composition at 100% activity, of an alpha olefin sulfonate anionic surfactant of general formula (I): $R^1$—CH═CH—$CH_2$—$SO_3^-M^+$ (I) in which $R^1$ is selected from linear or branched alkyl groups having from 11 to 13 carbon atoms and mixtures thereof; and M is a solubilizing cation; (ii) from 1 to 6%, by weight of an amphoteric or zwitterionic surfactant, selected from an alkyl betaine of general formula (II) $R^2$—$N^+(CH_3)_2$—$CH_2$—$COO^-M^+$ (II) wherein $R^2$═C12 (Lauryl) or Coco derived; an alkyl hydroxy sultaine of general formula (III), $R^3$—N+$(CH_3)_2$—$CH_2$—CH(OH)—$CH_2$—$SO_3^-M^+$ (III) wherein $R^3$═C12 (Lauryl) or Coco derived; an alkyl aminopropyl hydroxy sultaine of general formula (IV), $R^4$—CO—NH—$(CH_2)_3$—$N^+(CH_3)_2$—$CH_2$—CH(OH)—$CH_2$—$SO_3^-M^+$ (IV) wherein $R^4$═C12 (Lauryl) or Coco derived; an alkyl amphoacetate of general formula (V), $R^5$—CO—NH—$(CH_2)_2$—N($CH_2$—$CH_2$—OH)($CH_2$—$COO^-M^+$) (V) wherein $R^5$═C12 (Lauryl) or Coco derived; and mixtures thereof; (iii) from 0.05 to 0.9 wt % of a cationic conditioning polymer; (iv) from 0.05 to 10 wt % of a silicone emulsion; (v) a cationic deposition polymer; (vi) an inorganic electrolyte; and (vii) water in which the weight ratio of (i) to (ii) ranges from 1:1 to 6:1 and the pH of the composition is from 3 to 6.5.

17 Claims, No Drawings

(51) Int. Cl.
*A61K 8/89* (2006.01)
*A61Q 5/02* (2006.01)

(56) References Cited

U.S. PATENT DOCUMENTS

| | | | |
|---|---|---|---|
| 5,840,670 | A | 11/1998 | Payne et al. |
| 6,258,763 | B1 | 7/2001 | Arvanitidou et al. |
| 2006/0135397 | A1 | 6/2006 | Bissey-Beugras |
| 2012/0157365 | A1 | 6/2012 | Fevola |
| 2014/0349902 | A1* | 11/2014 | Allef ............ A61Q 19/10 510/491 |
| 2015/0093348 | A1* | 4/2015 | Sato ............ A61K 8/046 424/70.19 |
| 2015/0182438 | A1* | 7/2015 | Fujii ............ A61K 8/737 132/202 |
| 2015/0239993 | A1* | 8/2015 | Miyoshi ........ C08B 11/145 424/70.13 |
| 2016/0095804 | A1 | 4/2016 | Xavier et al. |
| 2017/0079899 | A1* | 3/2017 | Li ............ B08B 3/003 |
| 2017/0095410 | A1 | 4/2017 | Hara et al. |
| 2017/0151154 | A1* | 6/2017 | Scheunemann ....... A61K 8/64 |
| 2017/0319453 | A1* | 11/2017 | Ando ............ A61K 8/466 |
| 2017/0340540 | A1* | 11/2017 | Darras ............ A61K 8/44 |
| 2017/0360688 | A1* | 12/2017 | Fevola ............ A61Q 5/02 |
| 2018/0071198 | A1 | 3/2018 | Lin et al. |
| 2018/0243194 | A1* | 8/2018 | Mathonneau ........ A61K 8/86 |
| 2019/0224107 | A1* | 7/2019 | Lin ............ A61K 8/4993 |
| 2019/0314258 | A1 | 10/2019 | Laurent et al. |

FOREIGN PATENT DOCUMENTS

| | | |
|---|---|---|
| EP | 2897577 | 11/2020 |
| FR | 3021531 | 12/2015 |
| JP | 2016113383 | 6/2016 |
| JP | 2017226658 | 12/2017 |
| JP | 2017538707 | 12/2017 |
| WO | WO2012168126 | 12/2012 |
| WO | WO2018002557 | 1/2018 |

OTHER PUBLICATIONS

Disinfectant Concentrates as Additives in Various Compostions and Uses; IP.com; Mar. 20, 2008; pp. 1-68, XP13124304.

Search Report and Written Opinion in EP18171887; dated Nov. 12, 2018.

Search Report and Written Opinion in PCTEP2019061865; dated Jul. 1, 2019.

Deckner, "Then and Now: Shampoo Formulations through the Years", Prospector, https://knowledge.ulprospector.com/6253/pcc-shampoo-formulations-through-the-years; Apr. 7, 2017; 5 pages.

Search Report and Written Opinion in PCTEP2019061752; dated Jul. 5, 2019.

IRPR in PCTEP2019061865; dated Nov. 17, 2020; World Intellectual Property Org. (WIPO).

IPRP in PCTEP2019061752; dated Nov. 17, 2022; World Intellectual Property Org. (WIPO).

* cited by examiner

SULPHATE-FREE AND NONIONIC SURFACTANT-FREE CLEANSING COMPOSITION

CROSS-REFERENCE TO RELATED APPLICATIONS

This application is a U.S. National Stage Application under 35 U.S.C. § 371 of International Application No. PCT/EP2019/061752, filed on May 7, 2019, which claims the benefit of European Patent Application No. 18171879.2, filed May 11, 2018, the entire disclosures of which are hereby incorporated by reference for any and all purposes.

FIELD OF THE INVENTION

The subject invention relates to mild sulphate free cleansing compositions for hair and scalp.

BACKGROUND AND PRIOR ART

Microstructure and rheology are important factors in personal care formulations, as they affect consumer acceptance as well as product performance. The selection, amount and relative amount of surfactant contributes to the microstructure of a personal cleansing composition. In turn, microstructure can impact rheological properties such as composition viscosity and viscosity building characteristics, and may also contribute to composition stability.

A sufficient level of surfactant is ordinarily needed for surfactant molecules to be able to assemble into micelles, and for the micelles to aggregate to build structure. Commercially available water-based cleansing compositions frequently contain upwards of 12 weight percent of surfactant. The major surfactant component of such compositions is commonly an alkyl and/or alkyl ether sulfate surfactant, with lauryl and laureth sulfates, surfactants known to afford good detergency, being among the sulfate surfactants commonly employed. Sulfate surfactants belong to a class of materials known as anionic surfactants. The sulfate surfactants are frequently used together with an amphoteric co-surfactant, with betaine surfactants such as cocamidopropyl betaine being among the amphoteric surfactants commonly employed. Betaine surfactants help to boast lather and are generally milder than sulfate surfactants, albeit without the detergent power of the sulfate surfactants. Advantageously, personal cleansing compositions based on sulfate surfactant can normally be thickened by the addition of simple salts.

Despite the widespread use of sulfate surfactants in personal cleansing compositions, there is considerable interest in milder alternatives, including compositions in which the anionic surfactant is a sulfate free surfactant.

Achieving an acceptable composition viscosity is an important factor in providing a mild personal cleansing composition that can be applied in a controlled manner and readily spread in use. Composition viscosity, together with attributes such as foamability can also impact consumer perception of such products. When sulfate surfactants are eliminated, developing a microstructure that results in desirable rheological properties can be challenging, particularly in the case of mild compositions with low surfactant concentrations; additionally, building the viscosity of such compositions by the addition of a simple salt can be problematic. Eliminating sulfate surfactants can also be problematic in regard to formulating mild cleansing compositions that are stable at acidic pH.

One approach to the issue of thickening systems that are free of sulfate surfactants has been to use sulfate-free surfactants together with polymeric thickeners. Polymeric thickeners can have a gelation effect that transforms a product with what is ordinarily Newtonian rheology under conditions of low shear, such as is experienced, for example, during dosing, application and spreading in-use, to a non-Newtonian rheology. In addition to being detectable by a consumer as an undesirable departure from product norms, the use of such thickeners can further limit the ability to subsequently adjust composition viscosity through the use of simple salts.

Employing relatively high levels of non-sulfate surfactant may also assist in building the viscosity of systems that are free of sulfate surfactants. The levels of non-sulfate surfactant needed may, however, be higher than conventional norms, and may also result in non-isotropic surfactant systems having relatively non-labile liquid crystalline structures or domains. In contrast to isotropic surfactant systems, which tends to promote foaming efficiency, the relatively labile microstructure of liquid crystalline microstructures tend to "trap" surfactant and impair foamability. Additionally, liquid crystalline structures or domains may impede light transmission and may impart a turbid or cloudy appearance to a composition, which may be problematic where translucency is desired.

There is a need for mild sulphate free cleansing compositions, suitable for hair and scalp, having desirable rheological properties, including compositions with relatively low surfactant concentrations. Of particular interest are low surfactant content compositions free of sulfate surfactants, the viscosity of which compositions may be increased through the addition of electrolytes such as simple salts.

WO18002557A1 uses high concentrations (35-60%) of surfactant mixtures including sulfate free anionic, amphoteric and non-ionic that access the lamellar phase region to control the rheology. These formulas have no added salt. Although high surfactant concentrations in lamellar phase solve the rheology build problem, they may not favour mild benefits or have the in-use application and sensory characteristics of an isotropic shampoo, such as transparent appearance and flash foam.

US2017319453A teaches that a combination of Alpha Olefin Sulfonate (AOS) plus a glycerin fatty acid ester and an amphoteric surfactant (a betaine) give no irritation or reduced irritation, and superior foam quality, and may be stable, in particular stable over time and/or under elevated temperature. Under acidic pH, ester bonds are prone to attack and can become unstable, which tends to thin an isotropic formula over time. Heat will accelerate these destabilising reactions.

US2016095804A uses complex combinations of sulfate free surfactants (e.g. anionic surfactant plus amphoteric surfactants with optional non-ionic surfactants) but structures them with hydrophobically modified, high molecular weight polymers. It also employs cationic conditioning agents (mixtures of polymers and silicones or functional silicones). However, we have found that the addition of structuring polymers to a cleansing formula can result in adverse sensory performance in the form of poor clean feel, coating and stickiness.

US2017079899A & US2017095410A reveal that blends of Alpha Olefin Sulfonate with different chain lengths (C16+ C18) at high concentrations and at specific ratios require a suspending agent in the form of a polymeric material to thicken the formula. The use of amphoteric or zwitterionic materials such as betaines and the inclusion of at least one foam booster such as a fatty material are also envisaged.

US2012157365A uses a mixture of polyglyceryl nonionic, amphoteric and sulfate free anionic surfactants at pH less than 5.4 to employ organic acids such as sodium benzoate as the preservative. Ratios of polyglyceryl to amphoteric range from 0.05:1 to 3:1 and sulfate free anionic to amphoteric ranges from 0.3:1 to 4:1.

US2017/0340540 discloses cosmetic compositions, for cleansing and caring for keratinous substrates, comprising: (i) one or more linear tr.-olefin sulfonates, (ii) one or more non-oxyalkylenated anionic surfactants other than the compounds (i), present at 1% to 20% by weight; and (iii) one or more additional surfactants chosen from amphoteric surfactants and nonionic surfactants. An example includes alpha olefin sulphonate and cocobetaine along with 0.7 wt % of polyquaternium-10.

US2017/0360688 reveals the use of a combination of anionic and cationic polyelectrolytes in cosmetic compositions also containing at least one surfactant. Stable viscosity and yield stress are achieved.

Addition of silicone to a shampoo formulation is known to have a detrimental effect on the foaming properties, for example flash foam and foam height.

The inventors have identified Alpha Olefin Sulfonate (AOS) as a sulfate free, primary surfactant. As with sulfate based chassis a secondary surfactant is required to help build viscosity using salt, control the foam and aid in the delivery of mildness benefits through lower CMC.

It is desirable to reduce the level of surfactant used in formulations (for mildness and environmental benefits). We have found that if you reduce the amount of surfactant, then the viscosity of the formulation falls undesirably.

However, the typical secondary surfactant, cocamidopropyl betaine (CAPB) does not allow viscosity to be built at low total surfactant concentrations with Alpha Olefin Sulfonate (AOS) as the primary surfactant.

The inventors have now found that a combination of AOS, at a specified ratio, with at least one of an alkyl betaine, an alkyl hydroxy sultaine, an alkyl aminopropyl hydroxy sultaine or an alkyl amphoacetate can afford viscosity builds with salt addition at low total concentrations of surfactant. This negates the need for other thickening agents, for example, polymers and other secondary surfactants.

Compositions in accordance with the invention having a combination of anionic and amphoteric sulfate free surfactants at enriched amphoteric ratios; reduced surfactant concentrations; specific primary sulfate free surfactant levels, a cationic conditioning polymer and a silicone emulsion to provide good foamability, wet detangling, dry lubrication that provides silky, smooth feel and desirable rheological characteristics, whilst maintaining mildness to skin and hair protein.

Definition of the Invention

In a first aspect the present invention provides a sulphate free cleansing composition for hair and scalp comprising, in an aqueous continuous phase:
a total amount of anionic surfactant, amphoteric surfactant and zwitterionic surfactant consisting of:
(i) from 3 wt % to 13 wt %, by weight of the total composition at 100% activity, of an alpha olefin sulfonate anionic surfactant of general formula (I):

in which $R^1$ is selected from linear or branched alkyl groups having from 11 to 13 carbon atoms and mixtures thereof; and M is a solubilizing cation;
(ii) from 1 to 6%, by weight of an amphoteric or zwitterionic surfactant, selected from an alkyl betaine of general formula (II)

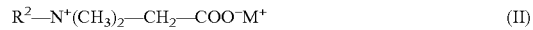

wherein $R^2$=C12 (Lauryl) or Coco derived;
an alkyl hydroxy sultaine of general formula (III),

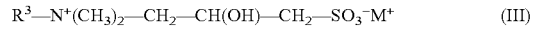

wherein $R^3$=C12 (Lauryl) or Coco derived;
an alkyl aminopropyl hydroxy sultaine of general formula (IV),

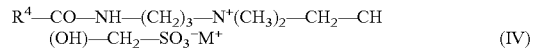

wherein $R^4$=C12 (Lauryl) or Coco derived;
an alkyl amphoacetate of general formula (V),

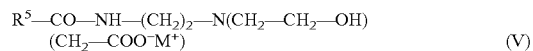

wherein $R^5$=C12 (Lauryl) or Coco derived;
and mixtures thereof;
(iii) from 0.05 to 0.9 wt % of a cationic conditioning polymer;
(iv) from 0.05 to 10 wt % of a silicone emulsion;
(v) a cationic deposition polymer;
(vi) an inorganic electrolyte; and
(vii) water;
in which the weight ratio of (i) to (ii) ranges from 1:1 to 6:1 and the pH of the composition is from 3 to 6.5.

In a second aspect, the invention provides a method of treating hair and/or scalp comprising the step of applying to the hair and/or scalp a composition as defined by the first aspect.

Preferably the method comprises an additional step of massaging the composition of the first invention into the hair and scalp.

Preferably the method comprises an additional step of rinsing the hair.

DETAILED DESCRIPTION OF THE INVENTION

All molecular weights as used herein are weight average molecular weights, unless otherwise specified.

Aqueous Continuous Phase

By "aqueous continuous phase" is meant a continuous phase which has water as its basis.

Suitably, the composition of the invention will comprise from about 75 to about 95%, preferably from 85 to 95%, more preferably from 87 to 95% water (by weight based on the total weight of the composition).

Preferably the composition comprises an isotropic surfactant phase, where under dilution, isotropic micelles provide higher availability of monomers to the air/water interface, whereas anisotropic may diffuse at a slower rate, resulting in lower flash foam properties. Thus, the isotropic phase is advantageous for product appearance, clarity and good flash foam properties.

All amounts referred to herein are based on 100% activity (or "active") unless otherwise stated. By 100% activity (or "active") is meant that the material is not diluted and is at 100% v/v or wt/wt. Many materials used in personal care formulations are commercially available at different active concentrations, for example at 70% active or 60% active.

For example, 100 ml of 70% active surfactant provides the same amount of active material as 70 ml of 100% active surfactant. Therefore, in order to provide for variations in activities of materials, all amounts are based on 100% active materials.

The aqueous continuous phase comprises a total amount of anionic, amphoteric and zwitterionic surfactant consisting of (i) and (ii) below. That is to say, no further anionic, amphoteric and zwitterionic surfactants are present in the compositions of the invention.

Preferably, no other surfactants, for example, nonionic surfactants are present in the compositions of the invention.

(i) The Alpha Olefin Sulfonate Anionic Surfactant

The composition of the invention comprises (i) one or more alpha olefin sulfonate anionic surfactants of general formula (I)

in which $R^1$ is selected from linear or branched alkyl groups having from 11 to 13 carbon atoms and mixtures thereof; and M is a solubilizing cation;

Preferably $R^1$ in general formula (I) is a $C_{14}$ or $C_{16}$ linear alkyl group.

Preferably M in general formula (I) is selected from alkali metal cations (such as sodium or potassium), ammonium cations and substituted ammonium cations (such as alkylammonium, alkanolammonium or glucammonium).

Commercially produced alpha olefin sulfonate anionic surfactants of general formula (I) may be made by sulfating C14-16 olefins derived from natural gas. The process can also yield mixtures of homologues and low levels of unreacted olefins.

Particularly preferred is alpha olefin sulfonate with an average of 14-16 carbons. A suitable example of such a material is Bioterge AS40 (ex Stepan).

The amount of alpha olefin sulfonate anionic surfactant, at 100% activity, of general formula (I) ranges from 3 to 13%, for example from 3 to 12.85%, preferably from 3.5 to 12%, more preferably from 3 to 10%, still more preferably from 3 to 9% and most preferably from 3.25 to 8% (by weight based on the total weight of the composition).

(ii) The Amophoteric or Zwitterionic Surfactant of General Formulae (II), (III), (IV) or (V)

The composition of the invention comprises (ii) an amphoteric or zwitterionic surfactant, selected from an alkyl betaine of general formula (II)

$$R^2-N^+(CH_3)_2-CH_2-COO^-M^+ \quad (II)$$

wherein $R^2$=C12 (Lauryl) or Coco derived;
an alkyl hydroxy sultaine of general formula (III), $$R^3-N^+(CH_3)_2-CH_2-CH(OH)-CH_2-SO_3^-M^+ \quad (III)$$

wherein $R^3$=C12 (Lauryl) or Coco derived;
an alkyl aminopropyl hydroxy sultaine of general formula (IV),

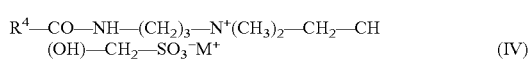

wherein $R^4$=C12 (Lauryl) or Coco derived;
an alkyl amphoacetate of general formula (V),

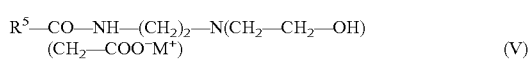

wherein $R^5$=C12 (Lauryl) or Coco derived;
and mixtures thereof.

The preferred surfactant (ii) is selected from coco betaine, lauryl hydroxy sultaine, coco aminopropyl hydroxy sultaine, lauryl amphoacetate and mixtures thereof, most preferably selected from coco betaine, lauryl hydroxy sultaine and mixtures thereof.

The amount of amphoteric or zwitterionic surfactants of general formula (II), (III), (IV) or (V) or mixtures thereof, preferably ranges from 1 to 6%, more preferably from 1 to 5%, most preferably from 1.2 to 4% (based on the total weight of the composition and 100% activity).

In a preferred composition according to the invention the amphoteric or zwitterionic surfactant (ii) is selected from coco betaine, lauryl hydroxy sultaine, coco aminopropyl hydroxy sultaine, lauryl amphoacetate and mixtures thereof, in an amount ranging from 1 to 4% (by weight based on the total weight of the composition and 100% activity).

In a more preferred composition the amphoteric or zwitterionic surfactant (ii) is selected from a betaine amphoteric surfactant of general formula (II), which is coco betaine, an amphoteric surfactant of general formula (III), which is lauryl hydroxy sultaine, and mixtures thereof, in an amount of from 1 to 4% (by weight based on the total weight of the composition and 100% activity).

An especially preferred composition according to the invention comprises (i) alpha olefin sulfonate in an amount ranging from 3.25 to 8% (by weight based on the total weight of the composition and 100% active material); and (ii) an amphoteric or zwitterionic surfactant selected from coco betaine, lauryl hydroxy sultaine, coco aminopropyl hydroxy sultaine, lauryl amphoacetate or mixtures thereof, in an amount ranging from 1 to 4% (by weight based on the total weight of the composition and 100% active material).

The combined amount of (i) and (ii) ranges from 4 to 19 wt %, preferably from 5 to 15 wt %, most preferably from 5 to 11 wt % (based on the total weight of the composition and 100% activity).

The weight ratio of the alpha olefin sulfonate anionic surfactant (i) to the amphoteric surfactant (ii) ranges from 1:1 to 6:1, preferably from 1.5:1 to 4.5:1 and most preferably 2:1 to 4:1.

The pH of the composition of the invention ranges from 3 to 6.5, preferably from 3.5 to 5.1, more preferably from 4 to 5.

A protonating agent may be used for achieving the low pH. Suitable protonating agents are acids. Suitable acids useful herein include hydrochloric acid, citric acid, acetic acid, tartaric acid, fumaric acid, lactic acid, malic acid, succinic acid, and mixtures thereof. Preferably, the acid is selected from the group consisting of citric acid, acetic acid, tartaric acid, hydrochloric acid, fumaric acid, lactic acid and mixtures thereof.

(iii) The Cationic Conditioning Polymer

The composition of the invention comprises (iii) one or more cationic conditioning polymers. Such polymers may enhance the delivery of wet feel benefits in the composition.

Cationic conditioning polymers for use in the invention suitably have a cationic charge density ranging from about 0.3 to about 4 meq/g, preferably from about 0.4 to about 3.5 meq/g. The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain. Cationic charge density can be determined according to the Kjeldahl Method. Those skilled in the art will recognize that the charge density of amino-containing polymers may vary depending upon pH and the isoelectric point of the amino groups. The charge density should be within the above limits at the pH of intended use.

Suitable cationic polymers for use in the invention include cationic polysaccharide derivatives, such as cationic cellulose derivatives and cationic starch derivatives.

Preferred cationic polysaccharide derivatives for use in the invention include cationic cellulose derivatives.

Examples of preferred cationic cellulose derivatives for use in the invention include poly(1,2-oxyethanediyl)-2-hydroxy-3-trimethylammonium propyl chloride cellulose ethers (INCI: Polyquaternium-10).

Preferably, the cationic conditioning polymer is selected from Polyquaternium 10, having a $M_w$ ranging from 800,000 to 2.5 million g/mol and a charge density ranging from 0.5 to 1.8 meq/g, and mixtures thereof.

Another class of suitable cationic conditioning polymers are the high molecular weight Polyethylene Glycol (PEG) polymers, for example PEG 45M, available as Polyox from Dow.

Mixtures of any of the above described polymers may also be used.

In preferred compositions according to the invention, the amount of cationic conditioning polymer (per se as active ingredient) ranges from 0.05 to 0.9%, more preferably from 0.1 to 0.6%, most preferably from 0.15 to 0.5% (by weight based on the total weight of the composition).

The Silicone

The composition of the invention comprises a silicone, in the form of an emulsion. Mixtures of silicones can be used.

The silicone is preferably selected from a silicone oil and a non-volatile silicone.

A suitable silicone is a silicone oil. For the purposes of the present invention, the term "silicone oil" means an oil which contains at least one silicon atom, and more particularly at least one Si—O group.

Examples of suitable silicone oils for use in the invention include linear or cyclic silicone oils having a kinematic viscosity of from about 0.65 to about 50, preferably from about 1.5 to about 5 cS ($mm^2 \cdot s^{-1}$) at 25° C. Example of such materials include linear or cyclic polydimethylsiloxanes having from 2 to 7 siloxane units, such as octamethylcyclotetrasiloxane, decamethylcyclopentasiloxane, dodecamethylcyclohexasiloxane, octamethyltrisiloxane, hexamethyldisiloxane, decamethyltetrasiloxane, dodecamethylpentasiloxane and their mixtures. Preferred are linear polydimethylsiloxanes having from 3 to 5 siloxane units and their mixtures. Such materials are commercially available for example as Dow Corning® 200 series fluids.

Another suitable silicone is a non-volatile silicone. The composition of the invention preferably includes emulsified droplets of non-volatile silicone having a mean droplet diameter (D3,2) of 1 micrometre or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

The term "non-volatile silicone" in the context of this invention means a silicone with a vapour pressure of less than 1000 Pa at 25° C.

Suitable silicones include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

All molecular weights as used herein are weight average molecular weights, unless otherwise specified.

Suitable silicones preferably have a kinematic viscosity of greater than 50,000 cS ($mm^2 \cdot s^{-1}$) and more preferably a kinematic viscosity of greater than 500,000 cS ($mm^2 \cdot s^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

When included, the amount of silicone in compositions of the invention may suitably range from 0.05 to 10%, preferably from 0.1 to 8%, more preferably 0.5 to 6.5%, most preferably 1 to 3% (by total weight 100% active silicone based on the total weight of the composition).

The Deposition Polymer

The composition of the invention includes a cationic deposition polymer which may be selected from cationic polygalactomannans having a mean charge density at pH7 from 0.2 to 2 meq per gram. Such polymers may serve to enhance the delivery of conditioning agents from the composition to the skin and/or hair surface during consumer use, thereby improving the conditioning benefits obtained. Mixtures of cationic deposition polymers may be employed.

The term "charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain.

The polygalactomannans are polysaccharides composed principally of galactose and mannose units and are usually found in the endosperm of leguminous seeds, such as guar, locust bean, honey locust, flame tree, and the like. Guar flour is composed mostly of a galactomannan which is essentially a straight chain mannan with single membered galactose branches. The mannose units are linked in a 1-4-β-glycosidic linkage and the galactose branching takes place by means of a 1-6 linkage on alternate mannose units. The ratio of galactose to mannose in the guar polymer is therefore one to two.

Suitable cationic polygalactomannans for use in the invention include polygalactomannans, such as guars, and polygalactomannan derivatives, such as hydroxyalkyl guars (for example hydroxyethyl guars or hydroxypropyl guars), that have been cationically modified by chemical reaction with one or more derivatizing agents.

Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted.

Preferred cationic polygalactomannans for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Cationic polygalactomannans for use in the invention (preferably guar hydroxypropyltrimethylammonium chlorides) generally have an average molecular weight (weight average molecular mass (Mw) determined by size exclusion chromatography) in the range 500,000 to 3 million g/mol, more preferably 800,000 to 2.5 million g/mol.

Cationic polygalactomannans for use in the invention generally have a charge density ranging from 0.5 to 1.8 meq/g.

Preferably the cationic polygalactomannans are selected from guar hydroxypropyltrimethylammonium chlorides having a charge density ranging from 0.5 to 1.8 meq/g (and mixtures thereof).

The cationic charge density of the polymer is suitably determined via the Kjeldahl method as described in the US Pharmacopoeia under chemical tests for nitrogen determination.

Specific examples of preferred cationic polygalactomannans are guar hydroxypropyltrimonium chlorides having a cationic charge density from 0.5 to 1.1 meq/g.

Also suitable are mixtures of cationic polygalactomannans in which one has a cationic charge density from 0.5 to 1.1 meq/g, and one has a cationic charge density from 1.1 to 1.8 meq per gram.

Specific examples of preferred mixtures of cationic polygalactomannans are mixtures of guar hydroxypropyltrimonium chlorides in which one has a cationic charge density from 0.5 to 1.1 meq/g, and one has a cationic charge density from 1.1 to 1.8 meq per gram.

Cationic polygalactomannans for use in the invention are commercially available from Solvay as JAGUAR @ C13S, JAGUAR @ C14 and JAGUAR @ C17. Also Esaflor OX 14B available from Lamberti.

In a preferred composition according to the invention the cationic polygalactomannans are selected from guar hydroxypropyltrimethylammonium chlorides having a charge density ranging from 0.5 to 1.8 meq/g (and mixtures thereof), at a level ranging from 0.15 to 0.2% by weight based on the total weight of the composition.

The cationic deposition polymer is preferably present in an amount of from 0.05 to 1 wt %, preferably from 0.1 to 0.5 wt %, most preferably from 0.15 to 0.2 wt % based on the total weight of the composition.

The Inorganic Electrolyte

We have found that, surprisingly, the compositions of the invention are amenable to building viscosity very well. It is thus possible to build viscosity at lower concentrations at enriched surfactant ratios. This is further advantage of the invention.

The composition of the invention includes at least one inorganic electrolyte. The inorganic electrolyte provides viscosity to the composition.

The viscosity of the composition suitably ranges from 2,500 to 25,000 mPa·s, preferably from 3,000 to 20,000 mPa·s, more preferably from 3,500 to 15,000 mPa·s, most preferably from 4,000 to 12,000 mPa·s when measured using a Brookfield V2 viscometer (spindle RTV5, 1 minute, 20 rpm) at 30° C.

At these ranges our products are pourable yet thick enough to satisfy the consumer desire for thick compositions.

Suitable inorganic electrolytes include metal chlorides (such as sodium chloride, potassium chloride, calcium chloride, magnesium chloride, zinc chloride, ferric chloride and aluminium chloride) and metal sulfates (such as sodium sulfate and magnesium sulfate).

It is intended that the inorganic electrolyte is separate from any inorganic electrolytes that may be present in the raw materials of the invention.

Examples of preferred inorganic electrolytes for use in the invention include sodium chloride, potassium chloride, magnesium sulfate and mixtures thereof.

Mixtures of any of the above described materials may also be suitable.

The amount of inorganic electrolyte in compositions of the invention preferably ranges from 0.5 to 10%, more preferably from 0.75 to 7%, even more preferably from 1 to 5% and most preferably from 1 to 3% (by weight based on the total weight of the composition).

A preferred composition of the invention has a weight ratio of (i) an alpha olefin sulfonate anionic surfactant of general formula (I) to (ii) an amphoteric or zwitterionic surfactant of general formula (II), (Ill), (IV), (V) or mixtures thereof, of from 2:1 to 4:1 and comprises an amount of inorganic electrolyte of from 1 to 3 wt % based on total weight of the composition.

A further preferred composition of the invention has a weight ratio of (i) an alpha olefin sulfonate anionic surfactant of general formula (I) to (ii) an amphoteric or zwitterionic surfactant of general formula (II), (Ill), (IV), (V) or mixtures thereof, of from greater than 4:1 to 6:1, preferably 5:1 to 6:1 and comprises an amount of inorganic electrolyte of from 1 to 5, preferably from greater than 3 to 5 wt %, more preferably 4 to 5 wt % based on total weight of the composition.

Preferably, the compositions of the invention are free from thickening agents selected from thickening polymers and secondary surfactants not included in (ii). In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of thickening agents by weight of the total composition. For the sake of clarity, the cationic polymer (iii) of the invention is not intended to be a thickening polymer.

A Preservative

The composition of the invention preferably comprises one or more preservatives, selected from sodium benzoate, sodium salicylate, benzyl alcohol, phenoxyethanol, 1,2- alkanediols, Iodopropynyl butylcarbamate (IPBC), 5-chloro-2-methyl-2H-isothiazol-3-one, 2-methyl-2H-isothiazol-3-one, or mixtures thereof. Preferably the preservative is an organic acid, most preferably the preservative is sodium benzoate.

A preferred composition has a pH of from 3 to 5, preferably 4 to 5 and comprises a preservative that is sodium benzoate.

Other Ingredients Preferably, the composition of the invention further comprises one or more structurants to assist in the suspension of dispersed benefit agent and provide phase stability. Suitable structurants include polyacrylic acids, polymethacrylic acids, cross-linked polymers of acrylic acid, cross-linked polymers of methacrylic acid, copolymers of acrylic acid with a hydrophobic monomer, copolymers of methacrylic acid with a hydrophobic monomer, copolymers of carboxylic acid-containing monomers and acrylic esters, copolymers of carboxylic acid-containing monomers and methacrylic esters, cross-linked copolymers of acrylic acid and acrylate esters, cross-linked copolymers of methacrylic acid and acrylate esters heteropolysaccharide gums and crystalline long chain acyl derivatives.

Preferred structurants are selected from polyacrylic acids, polymethacrylic acids, cross-linked polymers of acrylic acid, cross-linked polymers of methacrylic acid and mixtures thereof.

Mixtures of any of the above structurants may be used.

When included, the total amount of structurant is generally 0.1 to 10%, preferably from 0.1 to 3%, more preferably from 0.2 to 2%, most preferably from 0.3 to 0.9% (by weight based on the total weight of the composition).

A preferred composition comprises a structurant selected from polyacrylic acids, polymethacrylic acids, cross-linked polymers of acrylic acid, cross-linked polymers of methacrylic acid and mixtures thereof in an amount of from 0.1 to 10%, preferably from 0.1 to 3%, more preferably from 0.2 to 2%, most preferably from 0.3 to 0.9% (by weight based on the total weight of the composition).

A composition of the invention may contain further optional ingredients to enhance performance and/or consumer acceptability. Examples of such ingredients include fragrance, dyes and pigments. Each of these ingredients will be present in an amount effective to accomplish its purpose. Generally, these optional ingredients are included individually at an amount of up to 5% (by weight based on the total weight of the composition).

The composition of the invention is primarily intended for topical application to the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples.

EXAMPLES

Example 1: Preparation of Compositions 1 to 2 in Accordance with the Invention and Comparative Composition A Rinse-off aqueous hair cleansing shampoo formulations were prepared, having ingredients as shown in Table 1 below.

All the shampoos were prepared using the following method:

1. A vessel was charged with water. Surfactants and any structurant were added with stirring.
2. The mixture was heated to 30° C. and mixed until completely homogenous.
3. Any cationic polymer and silicone emulsion was then added and mixed well.
4. Any preservative was added.
5. The pH was adjusted to pH 4.5 using citric acid.
6. Salt was then added to adjust the viscosity.

TABLE 1

Compositions 1 and 2 in accordance with the invention and Comparative Composition A.

| INCI and/or Trade Name | % active | A | 1 | 2 |
| --- | --- | --- | --- | --- |
| Sodium Lauryl Ether Sulfate (Texapon N701) | 70 | 17.14 | | |
| Alpha Olefin Sulfonate (Bioterge AS-40) | 38.5 | | 19.09 | 19.09 |
| Cocamidopropyl betaine/Tego betain CK KB5 | 30 | 5.33 | | |
| Coco betaine/Genagen KB | 30 | | 8.83 | |
| Lauryl Hydroxy Sultaine/Mackam LHS E | 50 | | | 5.30 |
| Guar Hydroxypropyltrimonium Chloride | 100 | | 0.185 | 0.185 |
| Sodium Benzoate | 100 | 0.5 | 0.5 | 0.5 |
| Disodium Ethylenediamine-tetraacetic acid | 100 | 0.05 | 0.05 | 0.05 |
| Citric acid | 100 | too pH 4.5 | too pH 4.5 | too pH 4.5 |
| Sodium Chloride | 100 | 0.75 | 0.54 | 1.45 |
| Carbomer | 100 | | 0.3 | 0.3 |
| Perfume | 100 | | 0.5 | 0.5 |
| Dimethiconol/TEA-dodecylbenzene sulfonate | 50 | | 3 | 3 |
| PEG 45M | 100 | | 0.05 | 0.05 |
| Water | 100 | too 100% | too 100% | too 100% |

Example 2: Viscosity, Foaming and Deposition of Silicone Properties of Compositions 1 and 2 in Accordance with the Invention and Comparative Composition A The viscosities of the compositions given in Table 1 were measured using a Brookfield V2 viscometer (spindle RTV5, 1 minute, 20 rpm) at 30° C.

Flash foam and foam volume were measured using the following method:—

An oily soil (0.02 g) and shampoo (2 g) were added to a 250 ml measuring cylinder and made up to 20 g total with water.

The liquid was swirled (5 sec) to start the mixing of the shampoo.

The cylinder was inverted 10 times (in a steady, reproducible movement) and left for 30 s before the foam height was recorded (Flash Foam Reading).

The cylinder was then shaken 20 more times, left for 30 s and the foam height recorded.

Finally, the cylinder was shaken 30 more times, left for 30 s and the foam level recorded (Foam Volume Reading).

This was repeated three times for each shampoo formula and the average and standard deviation for each point calculated.

Silicone Deposition:

Virgin hair switches were treated with the compositions as follows:

Hair was washed with Composition 1, Composition 2 or Comparative Composition A using the following method:—

The hair switches were held under running water for 30 seconds, the composition applied at a dose of 0.1 ml of composition per 1 g of hair and rubbed into the hair for 30 seconds. Excess lather was removed by holding under running water for 30 seconds and the composition application repeated. The hair was rinsed under running water for 1 minute.

Switches were dried before the level of silicone was quantified using x-ray fluorescence (XRF).

TABLE 2

Viscosities, flash foam, foam volume and silicone deposition of Compositions 1 and 2 in accordance with the invention and Comparative Composition A.

|  | A | 1 | 2 |
|---|---|---|---|
| Viscosity, cP | 6694 | 4639 | 3830 |
| Flash Foam, ml | 76 | 67 | 64 |
| Foam Volume, ml | 117 | 102 | 105 |
| Amount of Si deposited/ppm |  | 2114 | 2556 |

It will be seen that the compositions of the invention provide excellent viscosity and foaming properties, despite the presence of a silicone.

The invention claimed is:

1. A sulphate-free cleansing composition for hair and scalp comprising, in an aqueous continuous phase:
   (A) a total amount of anionic surfactant, amphoteric surfactant and zwitterionic surfactant consisting of:
      (i) from 3 wt % to 13 wt %, by weight of the total composition at 100% activity, of an alpha olefin sulfonate anionic surfactant of general formula (I):

$$R^1-CH=CH-CH_2-SO_3^-M^+ \quad (I)$$

in which $R^1$ is selected from linear or branched alkyl groups having from 11 to 13 carbon atoms and mixtures thereof; and M is a solubilizing cation;
      (ii) from 1 to 6%, by weight of an amphoteric or zwitterionic surfactant, selected from the group consisting of:
   an alkyl betaine of general formula (II)

$$R^2-N^+(CH_3)_2-CH_2-COO^-M^+ \quad (II)$$

wherein $R^2$=C12 (Lauryl) or Coco derived;
   an alkyl hydroxy sultaine of general formula (III), $$R^3-N+(CH_3)_2-CH_2-CH(OH)-CH_2-SO_3^-M^+ \quad (III)$$

wherein $R^3$=C12 (Lauryl) or Coco derived;
   an alkyl aminopropyl hydroxy sultaine of general formula (IV), $$R^4-CO-NH-(CH_2)_3-N+(CH_3)_2-CH_2-CH(OH)-CH_2-SO_3^-M^+ \quad (IV)$$

wherein $R^4$=C12 (Lauryl) or Coco derived;
   an alkyl amphoacetate of general formula (V), $$R^5-CO-NH-(CH_2)_2-N(CH_2-CH_2-OH)(CH_2-COO^-M^+) \quad (V)$$

wherein $R^5$=C12 (Lauryl) or Coco derived;
   and mixtures thereof;
   (B) from 0.05 to 0.9 wt % of a cationic conditioning polymer;
   (C) from 0.05 to 10 wt % of a silicone emulsion;
   (D) a cationic deposition polymer;
   (E) an inorganic electrolyte; and
   (F) water;

wherein the weight ratio of (i) to (ii) ranges from 1:1 to 6:1 and the pH of the composition is from 3 to 6.5;
wherein the composition is free of nonionic surfactants;
wherein the composition is free of thickening polymers and secondary surfactants not defined in (ii); and
wherein the composition has a viscosity from 3,500 to 15,000 mPa·s when measured using a Brookfield V2 viscometer with spindle RTV5 for 1 minute at 20 rpm and 30° C.

2. The composition according to claim 1, wherein the amount of alpha olefin sulfonate anionic surfactant of general formula (I) is from 3 to 12.85% by weight based on the total weight of the composition and at 100% activity.

3. The composition according to claim 1, wherein the amount of amphoteric or zwitterionic surfactants of general formula (II), (III), (IV) or (V) is from 1 to 4% by weight based on the total weight of the composition and at 100% activity.

4. The composition according to claim 1, in which the combined amount of (i) and (ii) ranges from 5 wt % to 15 wt % by weight based on the total weight of the composition.

5. The composition according to claim 1, wherein the weight ratio of the alpha olefin sulfonate anionic surfactant (i) to the amphoteric or zwitterionic surfactant (ii) is from 1.5:1 to 4.5:1.

6. The composition according to claim 1, wherein the amphoteric or zwitterionic surfactant (ii) is selected from a betaine amphoteric surfactant of general formula (II), which is coco betaine, an amphoteric surfactant of general formula (III), which is lauryl hydroxy sultaine, and mixtures thereof, in an amount of from 1 to 4% by weight based on the total weight of the composition and 100% activity.

7. The composition according to claim 1, wherein the cationic polymer is selected from Polyquaternium 10, having a Mw ranging from 800,000 to 2.5 million g/mol and a charge density ranging from 0.5 to 1.8 meq/g, and mixtures thereof.

8. The composition according to claim 1, which has a viscosity from 4,000 to 12,000 mPa·s when measured using a Brookfield V2 viscometer with spindle RTV5 for 1 minute at 20 rpm and 30° C.

9. The composition according to claim 1, further comprising one or more preservatives, selected from the group consisting of sodium benzoate, sodium salicylate, benzyl alcohol, phenoxyethanol, 1,2-alkanediols, iodopropynyl butylcarbamate (IPBC), 5-chloro-2-methyl-2H-isothiazol-3-one, 2-methyl-2H-isothiazol-3-one and mixtures thereof.

10. The composition according to claim 1 which comprises an isotropic surfactant phase.

11. The composition according to claim 1, wherein the silicone is present in an amount of 0.5 to 6.5 wt %.

12. The composition according to claim 1, which comprises an amount of inorganic electrolyte of from 1 to 3 wt % based on total weight of the composition, and wherein the weight ratio of (i) to (ii) is from 2:1 to 4:1.

13. The composition according to claim 1, which comprises an amount of inorganic electrolyte of from greater than 1 to 5 wt %, based on total weight of the composition, and wherein the weight ratio of (i) to (ii) is from greater than 4:1 to 6:1.

14. A method of treating hair and scalp comprising the step of applying to the hair and scalp a composition as defined by claim 1.

15. The composition according to claim 2, wherein the amount of alpha olefin sulfonate anionic surfactant of general formula (I) is from 3.5 to 12% by weight based on the total weight of the composition and at 100% activity.

16. The composition according to claim 13, which comprises an amount of inorganic electrolyte of from greater than 1 to 5 wt %, based on total weight of the composition, and wherein the weight ratio of (i) to (ii) is from 5:1 to 6:1.

17. The composition according to claim 1, wherein the secondary surfactant comprises cocamidopropyl betaine.

* * * * *